(12) United States Patent
Higashitani et al.

(10) Patent No.: US 8,361,929 B2
(45) Date of Patent: Jan. 29, 2013

(54) METHOD OF RESTORING MALE STERILITY IN GRAMINEOUS PLANTS AND MALE STERILITY RESTORATIVE AGENT

(75) Inventors: Atsushi Higashitani, Sendai (JP); Masao Watanabe, Sendai (JP); Tadashi Sakata, Sendai (JP)

(73) Assignee: Tohoku University, Miyagi (JP)

( * ) Notice: Subject to any disclaimer, the term of this patent is extended or adjusted under 35 U.S.C. 154(b) by 0 days.

(21) Appl. No.: 13/179,048

(22) Filed: Jul. 8, 2011

(65) Prior Publication Data

US 2011/0306498 A1 Dec. 15, 2011

Related U.S. Application Data

(63) Continuation of application No. PCT/JP2010/050101, filed on Jan. 7, 2010.

(30) Foreign Application Priority Data

Jan. 8, 2009 (JP) .................................. 2009-002354

(51) Int. Cl.
- A01N 43/36 (2006.01)
- A01N 37/10 (2006.01)
- A01N 39/02 (2006.01)

(52) U.S. Cl. ........ 504/284; 504/314; 504/317; 504/321; 504/323

(58) Field of Classification Search .................. None
See application file for complete search history.

(56) References Cited

U.S. PATENT DOCUMENTS

| 6,239,073 B1* | 5/2001 | Back et al. ..................... 504/138 |
| 2011/0045976 A1* | 2/2011 | Villaverde Fernandez et al. ............................. 504/117 |

OTHER PUBLICATIONS

Abiko, Mafumi et al., "High-temperature induction of male sterility during barley (*Hordeum vulgare* L.) anther development is mediated by transcriptional inhibition," Sex Plant Reprod, 2005, vol. 18, pp. 91-100.

Oshino, Takeshi et al., "Premature progression of anther early development programs accompanied by comprehensive alterations in transcription during high-temperature injury in barley plants," Mol Genet Genomics, 2007, vol. 278, pp. 31-42.

Sakata, Tadashi et al., "Effects of High Temperature on the Development of Pollen Mother Cells and Microspores in Barley *Hordeum vulgare* L.," J. Plant Res., 2000, vol. 113, pp. 395-402.

Shimada, Atsumi et al., "Sterility in Rice Induced by Chemical Treatment," Biosci. Biotech. Biochem., 1992, vol. 56(10), pp. 1619-1622.

Tang, Ri-Sheng et al., "Possible correlation between high temperature-induced floret sterility and endogenous levels of IAA, GAs and ABA in rice (*Oryza sativa* L.)," Plant Growth Regul., 2008, vol. 54, pp. 37-43.

Wolbang, Carla W. et al., "Auxin from the Developing Inflorescence Is Required for the Biosynthesis of Active Gibberellins in Barley Stems," Plant Physiology, Feb. 2004, vol. 134, pp. 769-776.

Yin, Changxi et al., Decreased panicle-derived indole-3-acetic acid reduces gibberellin $A_1$ level in the uppermost internode, causing panicle enclosure in male sterile rice Zhenshan 97A, Journal of Experimental Botany, 2007, vol. 58, No. 10, pp. 2441-2449.

International Search Report for International Application No. PCT/JP2010/050101, dated Mar. 30, 2010, 1 page.

* cited by examiner

*Primary Examiner* — Alton Pryor
(74) *Attorney, Agent, or Firm* — Brinks Hofer Gilson & Lione

(57) ABSTRACT

The present invention provides a method and a composition for restoring pollen fertility by suppressing formation insufficiency in a pollen formation process due to a high-temperature or low-temperature stress. The present invention provides a fertility restorative agent comprising an auxin as an active ingredient, and a method for restoring the fertility of a plants of the family Poaceae, comprising spreading an auxin. Moreover, the present invention provides a fertility restorative agent containing as an active ingredient a substance which inhibits auxin action, and a method for restoring the fertility of rice plant, including spreading a substance which inhibits auxin action. Preferably, the auxin is $10^{-4}$ M to $10^{-7}$ M of indole-3-acetic acid (IAA), 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid or 2,4,5-trichlorophenoxyacetic acid.

9 Claims, 9 Drawing Sheets

THE EXPRESSION IS STRONGEST IN ANTHER (A) CONTROL GROUP (SUITABLE TEMPERATURE)
(B) ONE DAY AFTER HIGH-TEMPERATURE TREATMENT
(C) FIVE DAYS AFTER HIGH-TEMPERATURE TREATMENT
(D) SEVEN DAYS AFTER HIGH-TEMPERATURE TREATMENT (A) Control  (B) High temperature

AUXIN SPREADING: NO  YES  NO  YES

CONTROL GROUPS (SUITABLE TEMPERATURE)   HIGH-TEMPERATURE TREATED GROUPS

METHOD OF RESTORING MALE STERILITY IN GRAMINEOUS PLANTS AND MALE STERILITY RESTORATIVE AGENT

RELATED APPLICATIONS

This application is a continuation of PCT/JP2010/050101 filed on Jan. 7, 2010, which claims priority to Japanese Application No. 2009-002354 filed on Jan. 8, 2009. The entire contents of these applications are incorporated herein by reference.

BACKGROUND OF THE INVENTION

1. Field of the Invention

The present invention relates to a method for restoring sterility of a male sterile plant, such as a plant of the family Poaceae, particularly, a plant of the subfamily Pooideae, and to a composition for restoring sterility of a plant of the subfamily Pooideae. In particular, the present invention relates to a method and a composition for restoring sterility of a plant which becomes male sterile due to a high-temperature or low-temperature stress. Examples of the plant include plants of the family Poaceae, particularly, plants of the subfamily Pooideae.

2. Description of the Related Art

In the cases of plants of the subfamily Pooideae of the family Poaceae such as wheat and barley, temperature rise due to global warming or unusual weather causes formation insufficiency in the pollen formation process, which leads to worldwide decrease in crop production. Meanwhile, in the case of rice plant (*Oryza sativa*), as is known as the chilling injury in the Tohoku region, unusual low-temperature due to "Yamase," which is said to occur every approximately 10 years, causes formation insufficiency in the pollen formation process, and greatly lowers the yield.

In the low-temperature injury (chilling injury) of rice plant in the Tohoku region, anther wall tapetal cells become hypertrophic to inhibit pollen formation when the rice plant is exposed to such a low-temperature stress that the highest temperature is less than 20° C. for several days at the booting stage (immediately after the meiosis of pollen mother cells). The anther wall tapetal cells are cells that supply an influence to pollen and are destined to eventually collapse due to apoptosis.

Meanwhile, in contrast to rice plant, plants of the subfamily Pooideae such as wheat and barley are highly sensitive to a high-temperature stress. Cell division of anther wall cells and pollen mother cells stops under high-temperature conditions of 30° C. during the day and 25° C. at night (particularly, under a condition of 25° C. or above at night). If the high-temperature conditions continue for four days or longer, these plants turn into a completely non-restorable state. Anther wall tapetal cells collapse at an early stage. As a result, normal pollen cannot be formed, which results in pollen sterility (male sterility). This pollen sterility eventually leads to reduction in seed fertility. The stop of cell division and the collapse at an early stage are observed only in anthers. Such phenomena are observed only in male pollen formation, without affecting the growth of pistils, leaves, stems, and the like (Sakata et al., Journal of Plant Research (2000) 113, 395-402, and Abiko et al., Sexual Plant Reproduction (2005) 18, 91-100). An exhaustive expression analysis using a DNA microarray showed that large scale changes in gene expression occurred during the high-temperature injury. The expression of auxin repressed protein genes, whose expression is repressed by an auxin, is induced in high-temperature injury of young panicles (Oshino et al., Molecular Genetics and Genomics (2007) 278, 31-42). In other words, studies were made on the possibility that the expression of an auxin, which is one of the plant hormones and plays an important role in division, growth, development, and differentiation of cells, is reduced under a high-temperature condition in an anther-specific manner. Particularly, it is known that when the plant is placed in a high-temperature environment as described above at the start of the five-leaf stage, tapetal cells and pollen mother cells stop their development and differentiation and produce no pollen in anthers formed subsequently (Oshino et al., Molecular Genetics and Genomics (2007) 278, 31-42).

To solve these problems development is under way for cultivars which exhibit enhanced resistance to a high-temperature or low-temperature stress, by conventional breeding or by constructing recombinants through recombination technologies, for example.

An auxin is a generic term for plant hormones which promote mainly the growth of plants. Naturally occurring auxins and synthesis auxins are known. Naturally occurring auxins include indole-3-acetic acid (IAA) and indolebutyric acid (IBA). Synthesis auxins include 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid, 2,4,5-trichlorophenoxyacetic acid, and the like. These auxins have been used as growth control agents. Under laboratory environments, auxins are used for tissue culturing and the like. In farm fields, 2,4-D and the like are used as herbicides.

SUMMARY OF THE INVENTION

The present invention provides a method for restoring male sterility of a plant of the family Poaceae, particularly, male sterility due to a high-temperature or low-temperature stress, and a composition for restoring male sterility of a plant of the family Poaceae, particularly, male sterility due to a high-temperature or low-temperature stress.

The present invention provides a fertility restorative agent for a male sterile plant of the family Poaceae, particularly, for a plant of the subfamily Pooideae, comprising an auxin as an active ingredient, and a fertility restoration method for a male sterile plant of the family Poaceae, particularly, for a plant of the subfamily Pooideae, comprising spreading an auxin onto a plant.

More specifically, the present invention is as follows.

(1) A fertility restorative agent for a male sterile plant of the family Poaceae, which is adapted to be spread onto the plant of the family Poaceae at an auxin concentration of $10^{-4}$ M to $10^{-7}$ M (M: mol concentration).

(2) The fertility restorative agent according to (1), which is adapted to be spread at least once before or, at the latest, on a fifth-leaf development day in a young panicle stage.

(3) The fertility restorative agent according to (1), which is adapted to be spread at least once by the day before a fifth-leaf stage in a case where a night temperature is expected to reach 25° C. or above for consecutive three or more days starting from the fifth-leaf development day.

(4) The fertility restorative agent according to (1), which is adapted to be spread at least once in five days starting from a fifth-leaf development day.

(5) The fertility restorative agent according to any one of (1) to (4), wherein the auxin is indole-3-acetic acid (IAA), 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid or 2,4,5-trichlorophenoxyacetic acid.

(6) A method for restoring male sterility of a male sterile plant of the family Poaceae, comprising spreading an auxin onto the plant of the subfamily Pooideae at an auxin concentration of $10^{-4}$ M to $10^{-7}$ M.

(7) The method according to (6), wherein the auxin is spread at least once before or, at the latest, on a fifth-leaf development day in a young panicle stage.

(8) The method according to (6), wherein the auxin is spread at least once by the day before a fifth-leaf development day in a case where a night temperature is expected to reach 25° C. or above for consecutive three or more days starting from the fifth-leaf development day.

(9) The method according to (6), wherein the auxin is spread at least once in five days starting from a fifth-leaf development day.

(10) The method according to any one of (6) to (9), wherein the auxin is indole-3-acetic acid (IAA), 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid or 2,4,5-trichlorophenoxyacetic acid.

For the purpose of the present invention, the plants of the family Poaceae include plants of the family Poaceae and subfamily Pooideae. The plant of the subfamily Pooideae includes a plant of the genus *Hordeum*, the genus *Triticum*, the genus *Secale*, and the genus *Avena*.

Moreover, the present invention also provides a fertility restorative agent for a male sterile rice plant, comprising as an active ingredient a substance which inhibits auxin action, and a method for restoring fertility of a male sterile rice plant, using as an active ingredient a substance which inhibits auxin action. Examples of the substance which inhibits auxin action include aminooxyacetic acid (AOA), L-α-(2-aminoethoxyvinyl)glycine (AVG), p-chlorophenoxyisobutyric acid (PCIB), triiodoacetic acid (TIBA), and naphthylthalamic acid (NPA).

As used in the specification, the term "fertility restoration" from male sterility means that insufficiency in a pollen formation process is repressed in a plant, and an ability to form normal pollen is restored.

BRIEF DESCRIPTION OF THE DRAWINGS

FIG. 3(A) shows a period of a high-temperature treatment. FIG. 3(B) shows stages of young panicle development. At a fifth-leaf stage (when the tip of the fifth leaf had emerged), primordia (sp) of stamens and a primordium (pp) can be seen. At this stage, a high-temperature injury is most likely to occur.

FIG. 4(A) shows a correspondence between the high-temperature treatment period and the young panicle length. FIG. 4(B) shows meiosis of pollen mother cells and collapse of tapetal cells in a control group and a high-temperature treated group (where male sterility occurred). C10, C15, and C20 represent photomicrographs of stamens of the control group at stages of young panicle lengths of 10 mm, 15 mm, and 20 mm, respectively. H10, H15, and H20 are photomicrographs of stamens of the high-temperature experiment group at stages of young panicle lengths of 10 mm, 15 mm, and 20 mm, respectively.

FIG. 5(A) shows stamens and a pistil, as well as pollen in an anther of a control individual (suitable temperature cultivation) at a heading stage. FIG. 5(B) shows abnormal stamens and a pistil, as well as the lack of pollen grain formation in an anther of a high-temperature treated individual at a heading stage.

FIG. 9(A) an individual of a control group (suitable temperature cultivation), FIG. 9(B) an individual of a high-temperature treated group, and FIG. 9(C) individuals of experimental groups where a high-temperature treatment was conducted and auxins were spread at various concentrations.

DETAILED DESCRIPTION OF THE PREFERRED EMBODIMENTS

Figure 1:
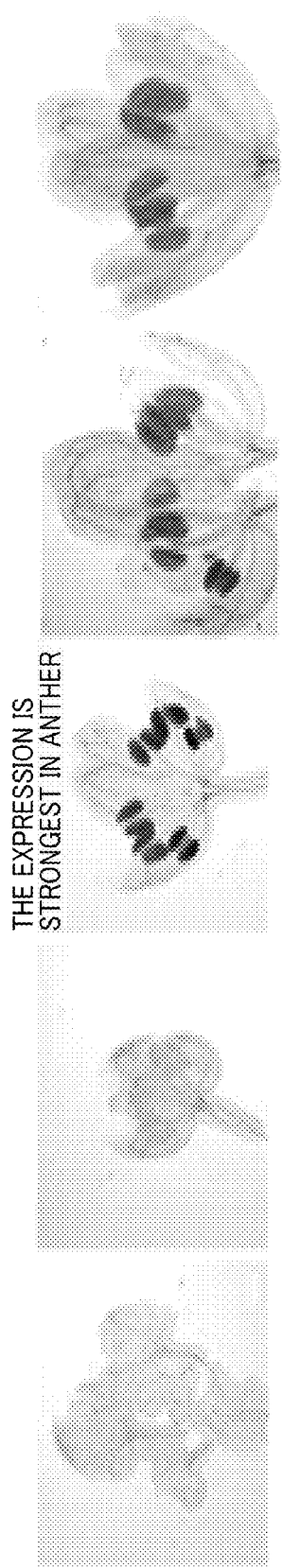
FIG. 1 shows the expression of an auxin responsive fused gene DR5-GUS in a flower development process of *Arabidopsis thaliana* under an appropriate cultivation condition. The expression was observed most strongly at an anther development stage.

Plants to which the present invention is suitably applied are plants in which an auxin level is greatly changed by a high-temperature or low-temperature stress, and in which the auxin level consequently influences greatly the pollen formation process. Examples of such plants include plants of the family Poaceae, in particular, plants of the subfamily Pooideae such as plants of the genus *Hordeum* (barley, and the like), plants of the genus *Triticum* (bread wheat, durum wheat, club wheat, spelt wheat, emmer wheat, and the like), plants of the genus *Secale* (rye, and the like), and plants of the genus *Avena* (oat, common wild oat, and the like); and rice plant.

In general, a high auxin activity is observed in the initial development process of anthers of monocotyledons including plants of the subfamily Pooideae and dicotyledons, but it has been revealed that the activity is remarkably lowered by high-temperature. As a result, it is believed that auxin deficiency occurs due to high-temperature and hence pollen mother cells and anther wall cells stop dividing and starts to collapse at an early stage, which finally leads to pollen sterility and decrease in seed fertility. Meanwhile, for the low-temperature injury of rice plant an auxin signal, which has to decrease along with normal maturation of anthers, does not decrease because of low-temperature and as a result, the collapse of the anther wall tapetal cells is inhibited, so that male sterility occurs.

Accordingly, when a high-temperature stress occurs in an anther development and differentiation process of a plant of the subfamily Pooideae such as wheat and barley, the anther-specific auxin deficiency, which is expected to be caused by the high-temperature stress, is compensated by exogenously spreading a substance having auxin action, so that the cell division, development, and differentiation of the pollen mother cells and the anther wall cells can be caused to proceed normally. Thus, the fertility of the male sterile plant of the subfamily Pooideae can be restored.

Meanwhile, when rice plant is exposed to a low-temperature stress during the anther development and differentiation process, the anther-specific excessiveness in auxin action, which is expected to be caused by the low-temperature stress, is cancelled by administering to rice plant a substance which inhibits auxin action, so that the collapse of the anther wall cells can be caused to proceed normally. As a result, the rice plant can be restored from male sterility.

In this description, a substance having a similar action to that of indole-3-acetic acid, which is a naturally occurring auxin, is generally referred to as an "auxin" or a "substance having auxin action." The auxin used in the present invention may be a naturally occurring auxin or a synthetic auxin. In this description, examples of the naturally occurring auxin include indole-3-acetic acid (IAA), and examples of the synthetic auxin include 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid, and 2,4,5-trichlorophenoxyacetic acid. The auxins usable in the present invention are not particularly limited, and all naturally occurring and synthetic auxins can be used. If there is a concern about the influence of the residual trace amount of auxin which has been spread onto a plant, IAA, which is naturally occurring and decomposes faster, is more preferably used than an artificial auxin 2,4-D which is not expensive but stable and resistant to decomposition from the viewpoints of safety and evaluation related to acceptance by consumers.

Meanwhile, examples of the substance which inhibits auxin action and which is used in the present invention include aminooxyacetic acid (AOA), L-α-(2-aminoethoxyvinyl)glycine (AVG), p-chlorophenoxyisobutyric acid (PCIB), triiodoacetic acid (TIBA), and naphthylthalamic acid (NPA).

Plants to which the present invention can be applied are plants which are likely to be male sterile due to high-temperature or low-temperature, particularly, plants which may be male sterile due to a high-temperature stress. Examples of such plants include, plants of the genus *Zea* of the family Poaceae (for example, maize), the genus *Solanum* of the family Solanaceae (for example, tomato, eggplant, capsicum pepper, bell pepper, and paprika), the genus *Vigna* of the family Fabaceae (for example, azuki bean (*V. angularis*) and cowpea), and the genus *Brassica* of the family Brassicaceae (for example, rapeseed), in addition to the plants of the family Poaceae, particularly, the plants of the subfamily Pooideae. Plants particularly suitable for restoring male sterility by the present invention are plants of the family Poaceae. Examples of the plants of the family Poaceae include rice plant, and plants of the subfamily Pooideae. Examples of the plants of the subfamily Pooideae include plants of the genus *Hordeum*, the genus *Triticum*, the genus *Secale*, and the genus *Avena*. Examples of the plants of the genus *Hordeum* include barley. Examples of the plants of the genus *Triticum* include bread wheat, durum wheat, club wheat, spelt wheat, and emmer wheat. Examples of the plants of the genus *Secale* include rye. Examples of the plants of the genus *Avena* include oat and common wild oat.

As a method for administering the auxin or the substance which inhibits auxin action to a plant of the subfamily Pooideae, it is preferable to spread onto a plants an aqueous solution thereof or a solution thereof using a solvent not so harmful to the plants, for example, to spread the solution onto the entirety or a portion of leaves and the epigeal stems. The spreading is preferably carried out by spraying (atomization). Alternatively, it is also possible to apply the auxin onto a portion of a petiole or a stem at which a young panicle is located. In the cases of barley and rice plant, it is not possible to spread the auxin directly onto a young panicle, because no young panicles have yet emerged at the time appropriate for spreading the auxin. However, in the cases where a young panicle is exposed at the appropriate time, it is also possible to directly spread or apply the auxin onto the young panicle. Moreover, particularly in the cases of dicotyledons, it is also possible to spread or apply the auxin directly onto an inflorescence or a flower bud exposed to the outside.

When the auxin is given in accordance with the present invention in order to restore the fertility of a plant of the family Poaceae, particularly, a plant of the subfamily Pooideae, the concentration of the auxin is preferably $10^{-4}$ M to $10^{-8}$ M, more preferably $10^{-4}$ M to $10^{-7}$ M, and particularly preferably $10^{-5}$ M to $10^{-6}$ M. In particular, in the cases of monocotyledons other than plants of the subfamily Pooideae, the concentration is more preferably $10^{-4}$ M to $10^{-7}$ M, and particularly preferably $10^{-5}$ M to $10^{-6}$ M. Since dicotyledons are generally more sensitive to the auxin than monocotyledons, the concentration is more preferably $10^{-5}$ M to $10^{-8}$ M, and particularly preferably $10^{-6}$ M to $10^{-7}$ M. If the concentration of the auxin spread is too high, auxin-induced ethylene synthesis occurs in the plants, and may lead to senescence or growth inhibition as an effect of the ethylene synthesis. Accordingly, when the concentration of the auxin to be spread is relatively high, it is also possible to add aminooxyacetic acid (AOA) or L-α-(2-aminoethoxyvinyl)glycine (AVG), which exhibits an effect of inhibiting the auxin-induced ethylene synthesis. As a result of this, side effects due to the auxin-induced ethylene synthesis can be reduced.

In some cases, it is possible to add a surfactant to the fertility restorative agent of the present invention in order to increase the spreadability of the fertility restorative agent of the present invention on a plant. Meanwhile, also when the auxin is administered to a plant of the family Poaceae in accordance with the present invention, it is possible to add a surfactant, for example, Tween 20, if needed. The concentration of the surfactant is preferably approximately 0.1% (v/v).

When the auxin is given to a plant of the family Poaceae in accordance with the present invention, it is preferable to administer the auxin during a period when the auxin level can influence the pollen formation. A preferable period for the auxin administration is generally a period from the stage where stamens start to differentiate or the stage where shoot apices start to differentiate into young panicles (around the fourth-leaf development stage) to the end of meiosis of pollen mother cells (around the sixth-leaf development stage) and to the microspore stage. The preferable period for the auxin administration can be clarified more precisely as follows. Specifically, for example, for each plant species or each plant cultivar, a genetically modified plant is produced by fusing a β-lucuronidase gene (GUS) into a transcription activation sequence DR5 responsive to an auxin. Then, the change with time in GUS activity is examined in the stamens, particularly the anthers of the genetically modified plant. Presumably, the period where the GUS activity significantly increases or decreases in the anthers is the appropriate time for the auxin administration. For plants for which a stamen differentiation starting time is not known, it is possible to determine a preferable period for the auxin administration as mentioned above. The genetically modified plant can be produced by a known method for each plant species. Alternatively, it is also possible to directly determine the auxin level in the anthers histologically and biochemically by using an anti-auxin antibody. An optimum auxin concentration for each plant species or each plant cultivar can be determined in a similar manner.

More specifically, for example, in the cases of plants of the subfamily Pooideae such as barley and wheat, it is preferable to administer the fertility restorative agent of the present invention or the auxin in accordance with the present invention at least once on or before a fifth-leaf development day in the young panicle stage. Particularly, high temperature at night is more likely to cause pollen sterility in plants of the subfamily Pooideae than high temperature during the day. Accordingly, it is particularly preferable to give the fertility restorative agent of the present invention or the auxin in accordance with the present invention at least once by the day before the fifth-leaf development in a case where the night temperature is expected to reach 25° C. or above for consecutive three or more days starting from the fifth-leaf development day. Moreover, it is preferable to give the fertility restorative agent of the present invention or the auxin in accordance with the present invention at least once in five days after the fifth-leaf development day. For example, it is preferable to perform the administration at least once on or before the fifth-leaf development day, and to further perform the administration to a plant of the family Poaceae several times in five days after the fifth-leaf development day. When a rapidly biodegradable auxin (for example, IAA) is used, the auxin may be spread every day. In addition, since individual plant species have their respective different adaptable ranges of temperature and concentration, it is preferable to use the fertility restorative agent or the auxin at an optimum concentration predetermined for each plant species or each plant cultivar as mentioned above, in a case where high-temperature injury is expected to occur under the conditions where the plant species or the plant cultivar is cultivated.

The low-temperature injury of rice plant is caused when rice plant is exposed to such a low-temperature stress that the highest temperatures is below 20° C. for several days at the booting stage (immediately after the meiosis of pollen mother cells). Accordingly, it is effective to spread a substance which inhibits an auxin activity when low-temperature is expected in a period immediately after the meiosis of pollen mother cells. Meanwhile, the treatment concentration of such a substance is the same as that employed in a known method in which the substance is used within a range where a physiological effect thereof can be exerted.

EXAMPLES

Example 1

1. Anther-Specific and Development-Specific Auxin Expression

By using *Arabidopsis thaliana*, which is one of the model plants, analysis was made as to anther-specific and development stage-specific auxin expression and anther-specific auxin decrease under high-temperature conditions.

For the experiment, a recombinant (Plant Cell 9, 1963-1971, 1997) was used as *Arabidopsis thaliana* into which a fused gene obtained by fusing a β-glucuronidase gene (GUS) into a transcription active sequence DR5 responsive to an auxin was introduced. This line expresses the fused gene DR5-β-glucuronidase in response to an auxin. This line was a gift from Dr. Tom Guilfoyle (University of Missouri, Columbia).

Approximately 10 to 20 seeds of the *Arabidopsis thaliana* of the DR5-GUS line were sown in a pot having a diameter of eight centimeters and they were grown in an incubator at 23° C. Approximately four weeks later, formation of flower buds started. The flower buds were sampled, and treated with acetone. Then, X-Gluc, which is a substrate of the β-glucuronidase, was caused to act thereon at a concentration of 2 mm, and thus cells expressing the β-glucuronidase (Gus) were detected. Under a condition of 23° C., a strong GUS expression (stained in blue-green) was observed in anther wall tapetal cells and pollen mother cells in a period from around the meiosis stage of pollen to the microspore stage (FIG. 1). After that, the GUS expression decreased starting from the stage of the collapse of anther wall tapetal cells, as the pollen formation proceeded. The GUS expression completely disappeared in mature pollen (FIG. 1). Specifically, a development stage-specific dynamic change was shown in which the auxin level in the anthers was highest at the anther development stage and gradually decreases in a process of disappearance of anther wall tapetal cells and maturation of pollen.

Plants grown at 23° C. and having flower buds were transferred to an incubator at 31° C. to conduct a high-temperature treatment and the GUS expression was induced with time. In a flower bud on Day 1 after the high-temperature treatment, the signals of anther wall tapetal cells and pollen mother cells were markedly weaken (FIG. 2(B)). When a high-temperature treatment was conducted for five days or seven days, the GUS signal in the anther completely disappeared (FIG. 2(C) and FIG. 2(D)). In addition, as a result of these, male sterility due to insufficient pollen formation occurred as in the case with barley.

Figure 2:
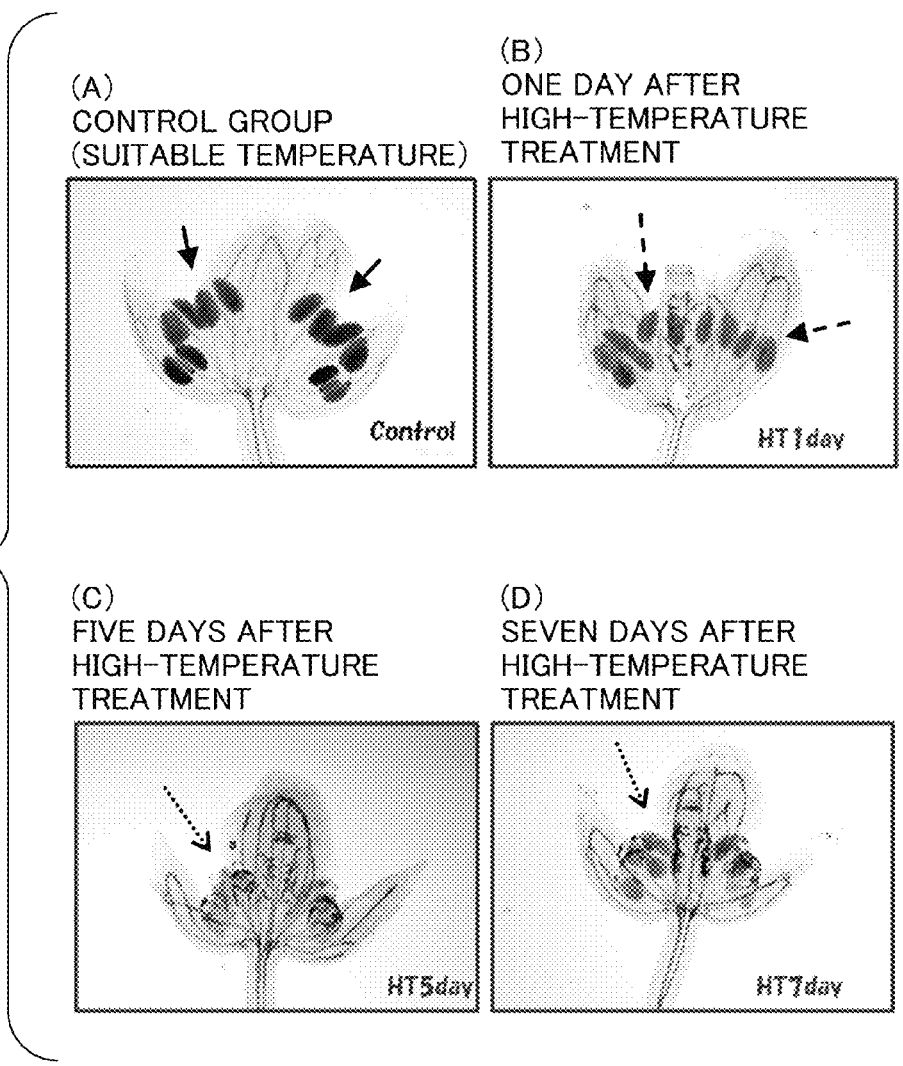
FIG. 2 shows fluctuation in expression of the auxin responsive fused gene DR5-GUS in *Arabidopsis thaliana* due to high-temperature. As the time elapses, remarkable decrease of GUS activity in anthers and GUS activity induction in pistils and petals are observed, FIG. 2(A) Control (suitable temperature cultivation), FIG. 2(B) Day 1 of high-temperature treatment, FIG. 2(C) Day 5 of high-temperature treatment, and FIG. 2(D) Day 7 of high-temperature treatment.

Meanwhile, it was found that the GUS expression signals increased by high-temperature in other tissues such as pistils and petals (FIG. 2). It has been reported so far that high-temperature increases an auxin expression signal in nutritionally growing tissues such as seedlings. The increases of expression in the pistils and the petals agree with this point, but high-temperature influences the development and differentiation process of anthers in stamens in a completely reversed manner. Presumably for this reason, a high-temperature injury occurs more remarkably in stamens.

2. Male Sterility Due to High-Temperature Stress in Barley

The barley used for the experiment was Haruna-nijo (*Hordeum vulagare* L. cv Haruna-nijo), a cultivar of two-row barley. Seeds having been stored in the dark at 4° C. were stimulated to germinate in the dark at 25° C. for 48 hours. Ten of the germinated seeds were sown in a circle in a round pot filled with one liter of a nursery soil for horticultural use (Zen-Noh Kureha culture soil: 0.4 g·kg$^{-1}$ of nitrogen, 1.9 g·kg$^{-1}$ of phosphoric acid, 0.6 g·kg$^{-1}$ of potassium, and 0.2 g·kg$^{-1}$ of magnesium) and having a diameter of 11 cm. These sown seeds were grown in an artificial climate chamber (Nippon Medical & Chemical Instruments Co., Ltd., BIOTRON LH-300 RDS) under conditions of 20° C. during the day, 15° C. at night, and a 16-hour photoperiod. As the light source, 20 plant growing fluorescent tubes were used (16 tubes; National, FL40S FR-P, and 4 tubes; National, FL20S FR-P). The day of the sowing was regarded as Day 0. The plants were grown under high-temperature conditions of 30° C. during the day, 25° C. at night, and a 16-hour photoperiod from Day 18 or 19 after the sowing when the fifth leaves appeared. Thus, a high-temperature treatment was conducted for five days (120 hours). Five days later, i.e., on Day 23 or 24 post-sowing, the conditions were changed back to cultivation conditions of 20° C. during the day and 15° C. at night, and the high-temperature treatment was terminated. The cultivation was continued to the subsequent panicle emergence and seed ripening.

Figure 3:
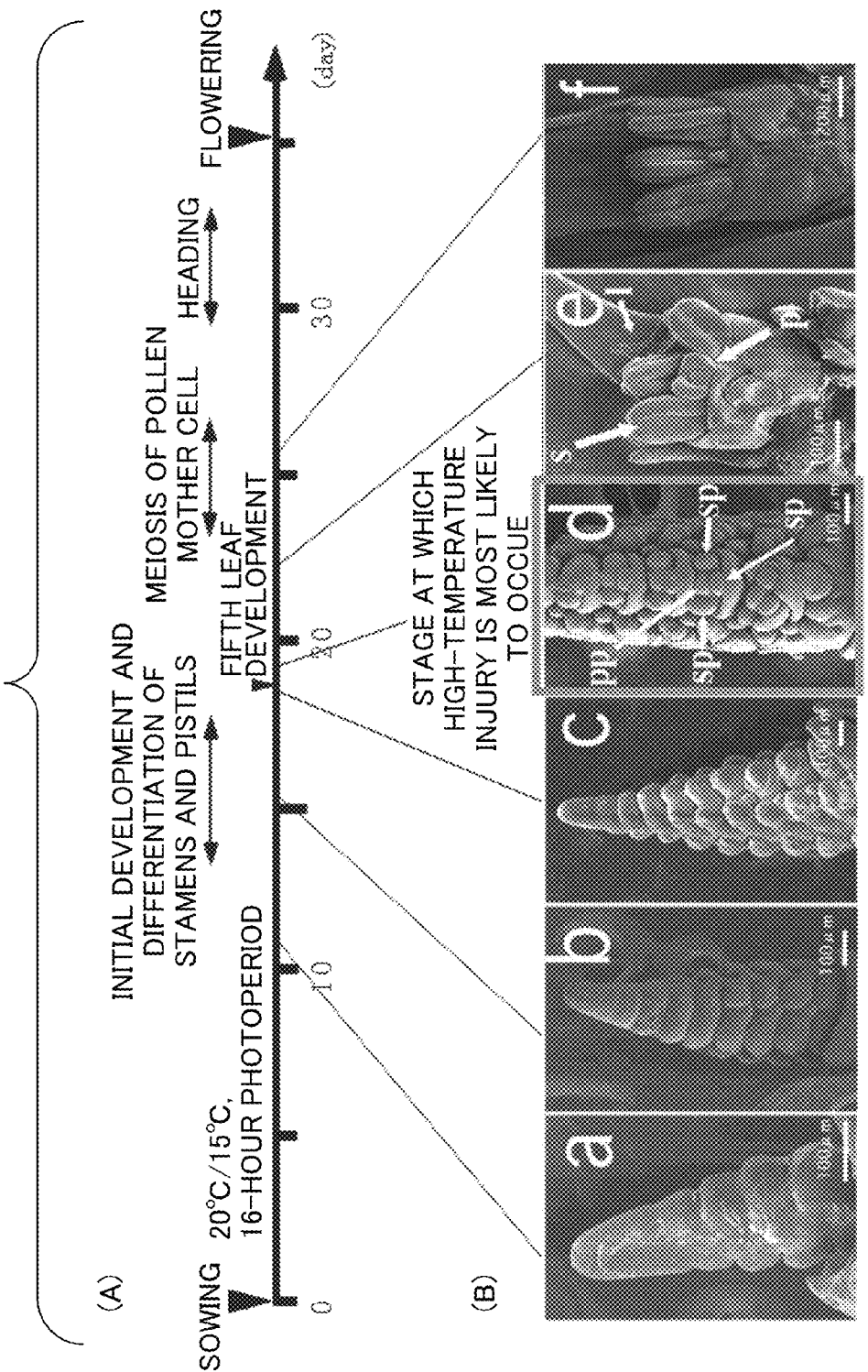
FIG. 3 shows development of young panicles observed in a reproductive growth process of barley.
Figure 4:
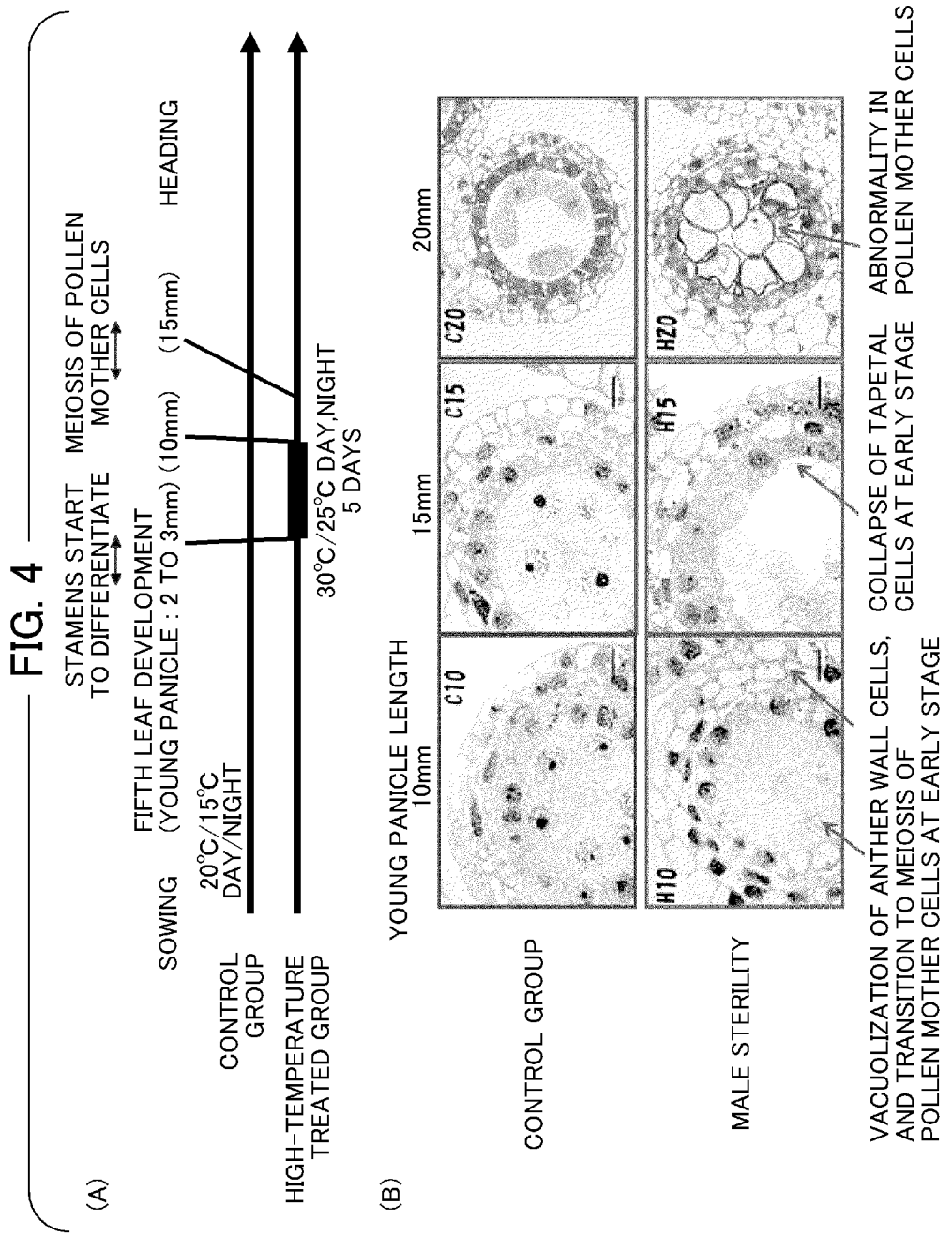
FIG. 4 shows a high-temperature injury observed in a stamen development process of barley. A high-temperature treatment was conducted from the fifth-leaf stage where young panicles grew to 2 to 3 mm, until the young panicles grew to about 10 mm.

In the case of barley, the young panicle length reaches 2 to 3 mm at the time of the fifth-leaf development, and primordia of stamens and pistils develop and differentiate in each glumous flower. Thereafter, reproductive growth proceeds successively (FIGS. 3 and 4). In five days from the fifth-leaf development, the young panicle length reaches about 10 mm, and anther wall cells are completed which are formed of four layers including tapetal cells. Then, the process transits to the meiosis of pollen mother cells. Thereafter, the meiosis of the pollen mother cells starts at a young panicle length of 15 mm. Pollen microspores are formed and anther wall tapetal cells proceed to collapse at a young panicle length of 20 mm. Five days are required for young panicles to grow from about 10 mm to 20 mm as described above.

Meanwhile, in a group subjected to a high-temperature treatment for the five days starting from the time of the fifth-leaf development, the increase in the young panicle length tends to be equal to or more promoted than that of a control group. However, the cell division stops at an early stage in the anther wall cells and the pollen mother cells. Moreover, the meiosis of the pollen mother cells in an immature state starts at a young panicle length of 10 mm, but pollen microspores also degenerate finally (FIG. 4).

Figure 5:
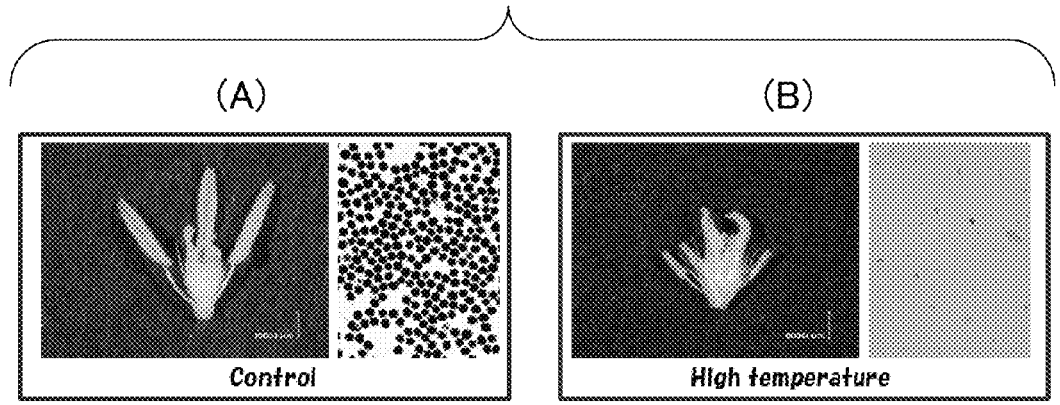
FIG. 5 shows an undeveloped anther and completely insufficient pollen formation observed when barley is exposed to high-temperatures of 30° C. during the day and 25° C. at night starting from a fifth-leaf stage for five days, and is then continued to be grown while the conditions are changed back to normal conditions of 20° C. during the day and 15° C. at night.

Under the high-temperature conditions, no abnormality occurs in development and differentiation of other tissues and organs including the pistils. As a result, anthers having no pollen at all are formed at the flowering stage, but pistils have fertility, so that complete male sterility (pollen failure) occurs (FIG. 5).

Figure 6:
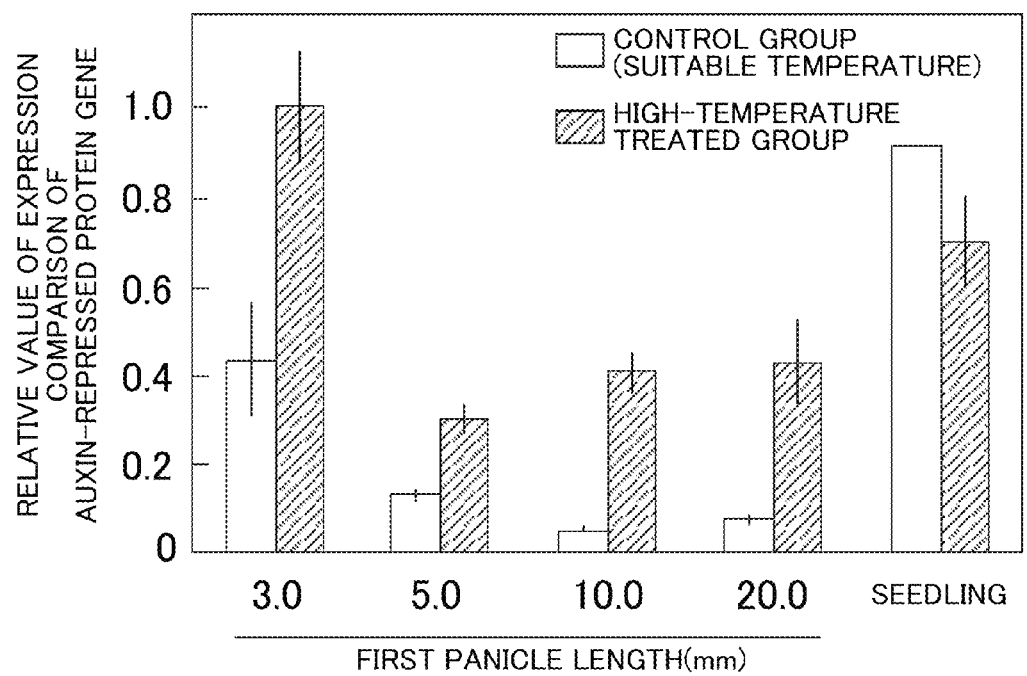
FIG. 6 shows the quantification results of the relative ratio of the gene expression level of an auxin-repressed protein gene of Contig 7516 at on a DNA microarray 22K Barley1 GeneChip (Affymetrix) at each young panicle length, the gene expression level determined by the real time RT-PCR method. The vertical axis represents the relative expression amount of the auxin-repressed protein gene, while the horizontal axis represents the young panicle length. Each outlined bar is for the control group (suitable temperature cultivation), whereas each black bar is for the high-temperature treated group. "Seedling" represents a change in expression of the gene due to the high-temperature treatment in a portion of an individual above the ground, the individual being obtained by subjecting an individual on Day 5 after the sowing to a similar high-temperature treatment for five days.

In these young panicles, significant upregulation of the expression of gene auxin-repressed protein genes was observed under the high-temperature conditions in comparison with the control group (FIG. 6). In other words, it was strongly suggested that, under high-temperature conditions, the auxin decreased also in barley, as in the case with *Arabidopsis thaliana*.

3. Restoration of Male Sterility Due to High-Temperature Stress by Auxin Treatment In an experiment to verify the effect of an auxin, the above-described nursery soil for horticultural was used. In addition, to facilitate the control of an auxin aqueous solution treatment, each pair of two rectangular planter boxes (60 mm×60 mm×100 mm (length×width×height), AGC TECHNO GLASS CO., LTD., Plant Box (Model No. CUL-JAR300)) were vertically stacked on each other. A hole having a diameter of about 1 cm was formed at the bottom center of the upper box. A 6-cm wick for an alcohol lamp with a knot was passed through the hole. Then, 300 ml of vermiculite (NIT-TAI Co., Ltd., vermiculite for agricultural and horticultural use) was packed thereabove. In the lower box, 0.2% (v/v) of HYPONEX (HYPONeX JAPAN CORP., LTD.) was placed as a nutrient water source for plants. Seeds of *Hordeum vulagare* L. cv Haruna-nijo having been stored in the dark at 4° C. were stimulated to germinate in the dark at 25° C. for 48 hours. The germinated seeds were sown at four seeds per pot at the four corners of the upper container. These sown seeds were grown in an artificial climate chamber (Nippon Medical & Chemical Instruments Co., Ltd., BIOTRON LH300RDS) under conditions of 20° C. during the day, 15° C. at night, and a 16-hour photoperiod. As the light source, 20 plant growing fluorescent tubes were used (16 tubes; National FL40S FR-P, and 4 tubes; National, FL20S FR-P).

Also in this cultivation method, the fifth leaves emerge and start to develop on Day 18 or 19 after the sowing as in the case where the culture soil was used, where the day of the sowing is regarded as Day 0. The plants were cultivated under high-temperature conditions of 30° C. during the day, 25° C. at night, and a 16-hour photoperiod from Day 19 after the sowing. Thus, a high-temperature treatment was conducted for five days (120 hours). Thereafter (on Day 24 after the sowing), the conditions were changed back to the normal conditions of 20° C. during the day, 15° C. at night, and a 16-hour photoperiod.

First, $10^{-3}$ M, $10^{-2}$ M, and $10^{-1}$ M stock solutions in dimethyl sulfoxide (DMSO: Wako Pure Chemical Industries, Ltd., Production Code: 043-07216) were prepared by using each of indole-3-acetic acid (IAA: Wako Pure Chemical Industries, Ltd., Production Code: 94-00183), 1-naphthyl acetic acid (NAA: Wako Pure Chemical Industries, Ltd., Production Code: 148-00092), and 2,4-dichlorophenoxyacetic acid (2,4-D: Wako Pure Chemical Industries, Ltd., Production Code: 040-18532). The stock solutions were stored in the dark at −20° C. until used. These stock solutions were thawed immediately before spread, and each were diluted 1000-fold with distilled water. Thus, solutions were prepared at three levels of $10^{-6}$ M, $10^{-5}$ M, and $10^{-4}$ M, and used as auxin aqueous solutions. At this time, a reagent equivalent to Tween 20 (Polyoxyethylene (20) Sorbitan Monolaurate (a product equivalent to Tween 20, a trade name of ICI): Wako Pure Chemical Industries, Ltd., Production Code 167-11515) was added as a surfactant at a concentration of 0.1% (v/v). As a control group against auxin treated groups, a mixture liquid was prepared which contained DMSO and the surfactant at concentrations of 0.1% (v/v), respectively, and spread to the plants. The spreading onto the plants was carried out within 30 minutes after the stock solutions were diluted with distilled water.

Figure 7:
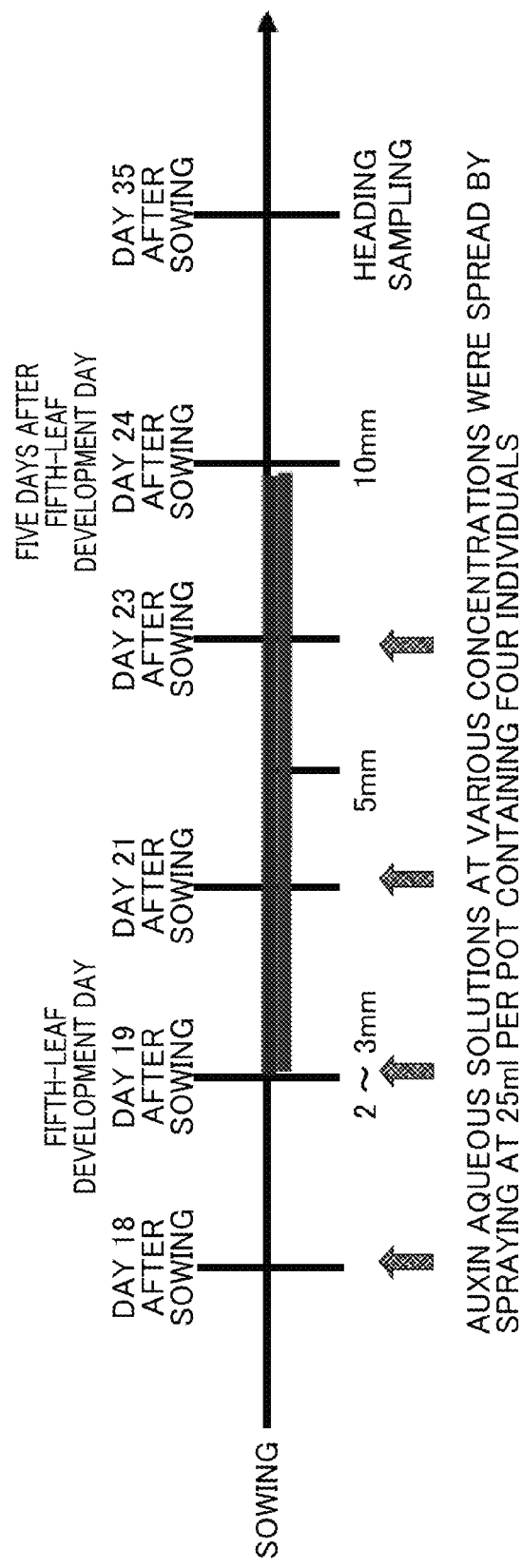
FIG. 7 shows a high-temperature treatment period at the fifth leaf stage of barley. Each auxin aqueous solution at various concentrations was spread onto plants at 25 ml per pot (four individuals). The auxin aqueous solutions were spread on Days 18, 19, and 21 after the sowing.

The auxin aqueous solutions were spread onto the plants four times in total, i.e., on Day 18 (the day before the high-temperature treatment), Day 19 (immediately before the high-temperature treatment), Day 21 (during the high-temperature treatment), and Day 23 (during the high-temperature treatment) after the sowing (FIG. 7). In the spreading of the auxin aqueous solutions during the high-temperature treatment, each auxin aqueous solution was spread by spraying almost uniformly onto the entire leaves and stems above the ground, and the plants were returned to the artificial climate chamber as soon as possible, within ten minutes from the time the plants were taken out from the artificial climate chamber. The amount of each auxin aqueous solution spread was 25 ml per pot (approximately 6 ml per individual of barley).

Three glumous flowers before flowering and pollination were sampled from each of barley panicles which emerged from Day 33 to Day 40 after the sowing. These panicles were subjected to fixation in an FAA fixative solution (5% formaldehyde, 5% acetic acid, 45% ethanol, and 45% $H_2O$) at 4° C. in the dark for 24 hours, and were finally immersed in a 0.1M phosphate buffer (pH 7.2) and stored at 4° C.

Stamens and pistils were dissected from the fixed glumous flowers under a stereomicroscope (OLYMPUS SZX12), and digitally photographed with a microscope camera (OLYMPUS DP70). The length of each anther was measured based on the digital image by using image processing software Image J (for measurement of anther size, freely distributed by the National Institutes of Health). For each concentration of each auxin, nine seeds from three individuals (three seeds per individual) were observed, and the sizes of three anthers present in each seed were measured. Then, an average value and a standard error thereof were found (approximately 27 anthers were measured per concentration treated group). To investigate the maturity of pollen, three anthers were stained per concentration treated group with a potassium iodide staining solution (manufactured by MERCK, Lugol's solution (Product number: 109261)), and were subjected to pollen observation using a microscope (OLYMPUS BX51) and digitally photographed with a microscope camera (OLYMPUS DP70).

In the heading stage of barley, the normal anther length is around 3 mm. In the control groups in the experiment, change was hardly observed in all the cases of spreading the auxin IAA, 2,4-D, or NAA at a concentration of $10^{-6}$ M, $10^{-5}$ M, or $10^{-4}$ M. Moreover, the pollen was also formed normally. However, in the $10^{-4}$ M 2,4-D-treated group, leaves stared to wither at an early stage, indicating that a negative effect on the plants was caused by the auxin.

Figure 8:
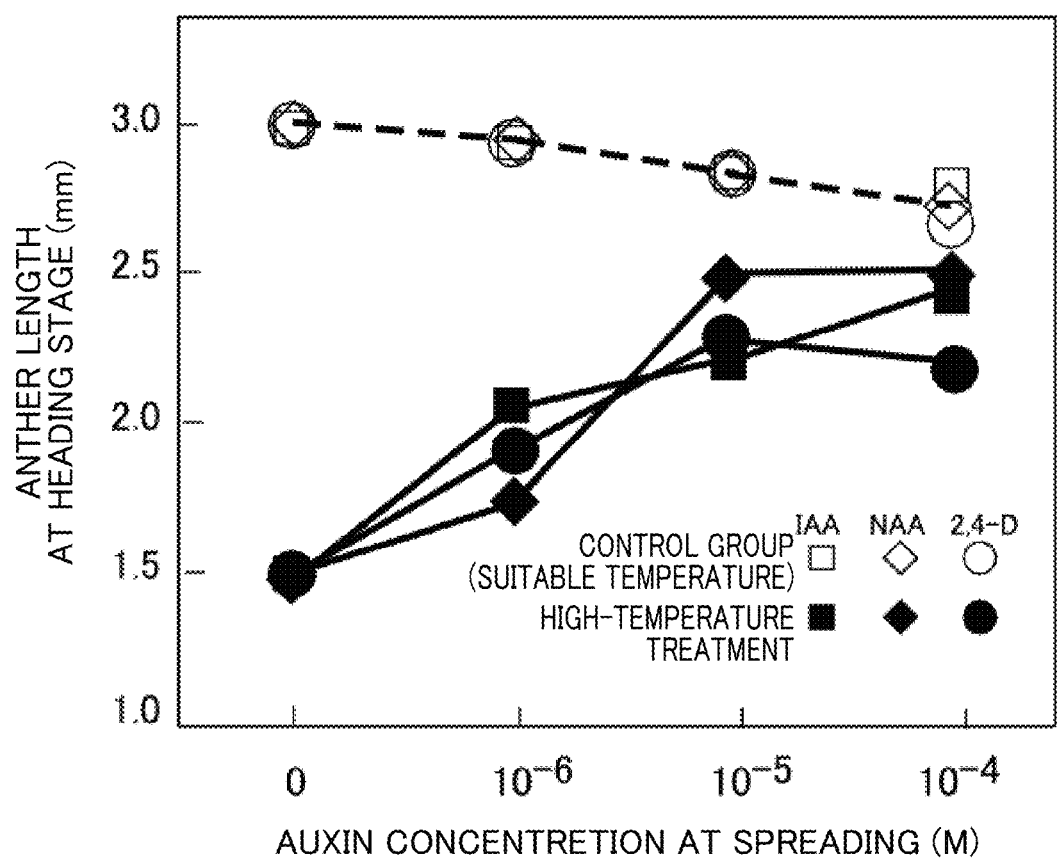
FIG. 8 shows anther length restoration achieved by spreading the auxin aqueous solutions at a heading stage. Dotted lines represent control groups (suitable temperature cultivation), and solid lines represent high-temperature treated groups.
Figure 9:
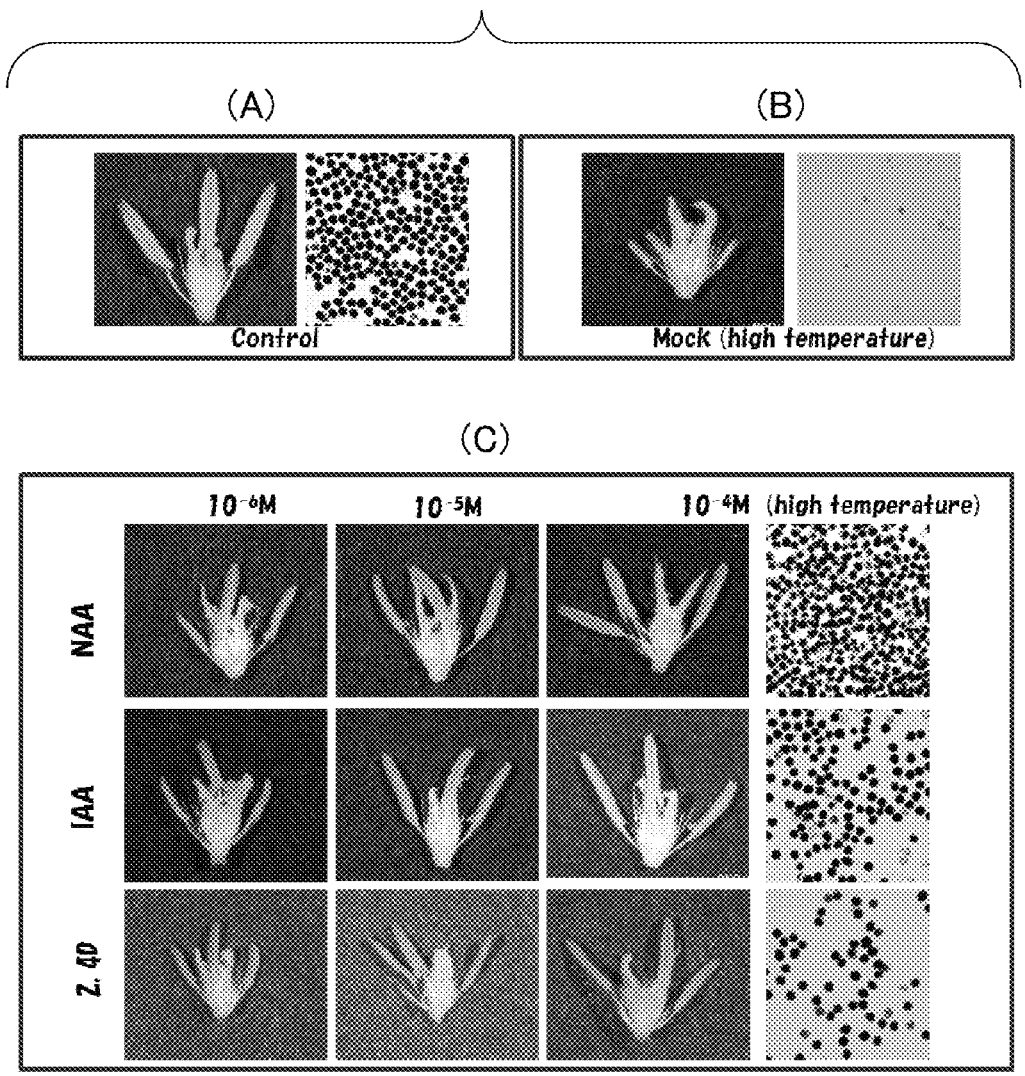
FIG. 9 shows examples of morphologies of stamens and pistils and restoration of pollen fertility at the heading stage achieved by spreading auxin aqueous solutions.

Among the high-temperature treated groups, in a case where only the mixture liquid containing DMSO and the surfactant at concentrations of 0.1% (v/v), respectively, and water were spread as a control against auxin effects, the growth of anthers was remarkably inhibited at the heading stage, so that the anther length grew to only about 1.5 mm (FIG. 8). Moreover, normal pollen grains were not observed at all inside the anthers (FIG. 9(B)). As in the cases where nothing was spread, no restorative effect was obtained. The anther length grew to about 1.8 mm to 2 mm in the cases of spreading $10^{-6}$ M IAA, 2,4-D, or NAA. The anther length grew up to around 2.5 mm in each case of spreading a $10^{-5}$ M or $10^{-4}$ M auxin aqueous solution. These results revealed that significant restoration was achieved even under high-temperature conditions (FIG. 8). Moreover, the inside of an anther whose anther length was restored by any one of $10^{-6}$ M, $10^{-5}$ M, and $10^{-4}$ M auxin treatments was stained in dark purple with the potassium iodide staining solution, indicating that normal mature pollen having sufficient starch accumulated therein was formed (FIG. 9(C)). As mentioned above, in the case of high-temperature treated samples, leaves started to wither at an early stage in the $10^{-4}$ M 2,4-D-treated group, indicating that a negative effect on the plants was caused by the auxin. However, in the cases of IAA or NAA, side effects were hardly observed even at $10^{-4}$ M.

Figure 10:
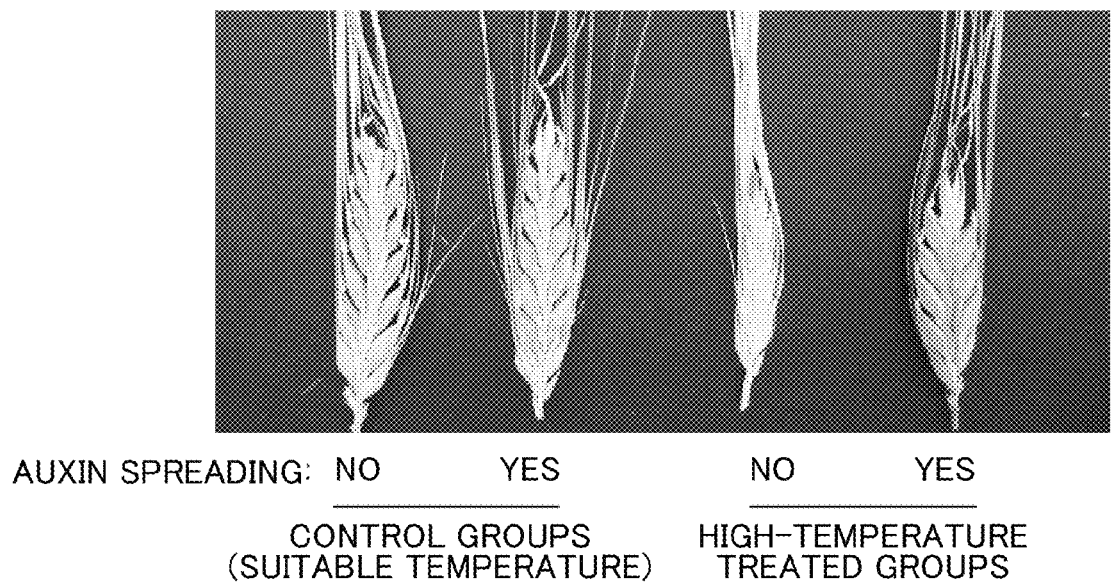
FIG. 10 shows an example of seed fertility restoration by spreading an auxin. An auxin (NAA) was spread at $10^{-4}$ M onto an individual of each of a control group (suitable temperature cultivation) and a high-temperature treated group. The two photographs on the left show seed fertility restoration in an individual of a high-temperature treated group by the auxin.

In nature, barley is self pollinated in almost all cases. As a result, in the high-temperature treated groups, panicle emergence was observed, but no pollination is accomplished, so that no seeds are produced (FIG. 10). Meanwhile, seeds were produced under high-temperatures in any of the auxin treated groups of this time where the pollen fertility was restored (except the $10^{-4}$ M 2,4-D treated group of the withering up at the early stage). Seeds were produced in panicles at about 30% to 80% in each of the cases of all the auxins at $10^{-6}$ M, at about 70% to 85% in each of the $10^{-5}$ M treated groups of all the auxins, and at about as high as 90% in each of the $10^{-4}$ M IAA and NAA treated groups, so that it was also verified that the seed fertility was successfully restored (FIG. 10).

In addition, it was demonstrated that significant fertility restorative effect was observed even when an auxin was spread only once as in the initial case, and that a high-temperature injury was avoidable by an auxin treatment in a totally similar manner even in a case of cultivation using a culture soil for horticultural use.

What is claimed is:

1. A method for restoring male sterility of a male sterile plant of the family Poaceae, comprising spreading an auxin onto the plant of the family Poaceae at an auxin concentration of $10^{-4}$ M to $10^{-7}$ M.

2. The method according to claim 1, wherein the auxin is spread at least once before or, at the latest, on a fifth-leaf development day in a young panicle stage.

3. The method according to claim 1, wherein the auxin is spread at least once by the day before a fifth-leaf development day in a case where a night temperature is expected to reach 25° C. or above for consecutive three or more days starting from a fifth-leaf development day.

4. The method according to claim 1, wherein the auxin is spread at least once in five days starting from a fifth-leaf development day.

5. The method according to any one of claims 1 to 4, wherein the auxin is indole-3-acetic acid (IAA), 4-chloroindoleacetic acid, phenylacetic acid, 2,4-dichlorophenoxyacetic acid (2,4-D), α-naphthaleneacetic acid (NAA), 2,6-dichlorobenzoic acid, indolebutyric acid (IBA), 4-chlorophenoxyacetic acid, ethyl 5-chloroindazoleacetate, naphthoxyacetic acid or 2,4,5-trichlorophenoxyacetic acid.

6. The method according to any one of claims 1 to 4, wherein the plant of the family Poaceae is a plant of the subfamily Pooideae.

7. The method according to claim 6, wherein the plant of the subfamily Pooideae is a plant of the genus *Hordeum*, the genus *Triticum*, the genus *Secale*, or the genus *Avena*.

8. The method according to claim 5, wherein the plant of the family Poaceae is a plant of the subfamily Pooideae.

9. The method according to claim 5, wherein the plant of the family Poaceae is a plant of the subfamily Pooideae, and the plant of the subfamily Pooideae is a plant of the genus *Hordeum*, the genus *Triticum*, the genus *Secale*, or the genus *Avena*.

* * * * *